United States Patent [19]

Bisabri-Ershadi et al.

[11] Patent Number: 4,868,215
[45] Date of Patent: Sep. 19, 1989

[54] SUBSTITUTED N-AROYL N'-PHENYL UREA COMPOUNDS

[75] Inventors: Barat Bisabri-Ershadi, Pittsburgh, Calif.; Raymond H. Rigterink, Midland, Mich.

[73] Assignee: The Dow Chemical Company, Midland, Mich.

[21] Appl. No.: 653,642

[22] Filed: Sep. 24, 1984

Related U.S. Application Data

[63] Continuation of Ser. No. 401,493, Jul. 26, 1982, abandoned.

[51] Int. Cl.$^4$ ............... C07C 127/22; A01N 47/34
[52] U.S. Cl. ............... 514/594; 544/335; 546/278; 560/18; 560/34; 564/23; 564/44
[58] Field of Search ............... 560/18, 34; 260/465 D; 564/23, 44; 544/335; 546/278; 424/251, 263, 273, 304, 309, 310, 322

[56] References Cited

U.S. PATENT DOCUMENTS

| | | | |
|---|---|---|---|
| 3,748,356 | 7/1973 | Wellinga | 260/553 |
| 3,933,908 | 1/1976 | Wellinga | 260/553 |
| 4,013,717 | 3/1977 | Wellinga | 260/553 |
| 4,089,975 | 5/1978 | Wade | 564/44 |
| 4,139,636 | 2/1979 | Sirrenberg | 564/44 |
| 4,139,686 | 2/1979 | Jabs | 521/121 |
| 4,162,330 | 7/1979 | Ehrenfreund | 564/44 |
| 4,276,310 | 1/1981 | Sirrenberg | 424/322 |
| 4,277,499 | 7/1981 | Sirrenberg | 424/322 |
| 4,348,412 | 9/1982 | Ehrenfreund | 564/44 |

FOREIGN PATENT DOCUMENTS

| | | |
|---|---|---|
| 14674 | 8/1980 | European Pat. Off. |
| 14675 | 8/1980 | European Pat. Off. |
| 14676 | 8/1980 | European Pat. Off. |
| 14881 | 9/1980 | European Pat. Off. |
| 2726684 | 1/1979 | Fed. Rep. of Germany |
| 1460410 | 1/1977 | United Kingdom |
| 1460418 | 1/1977 | United Kingdom |
| 1460419 | 1/1977 | United Kingdom |
| 1501607 | 2/1978 | United Kingdom |

Primary Examiner—Michael L. Shippen

[57] ABSTRACT

N-aroyl N'-phenyl ureas having the formula

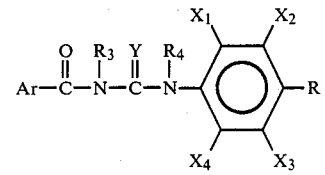

wherein: Ar is a substituted phenyl, pyridyl or pyrimidinyl radical wherein the substituents are chloro, bromo, fluoro $C_1$–$C_3$ alkyl or $C_1$–$C_3$ alkoxy, with the proviso that at least one substituent is positioned ortho to the carbonyl group; $R_3$ and $R_4$ are individually H or $C_1$–$C_4$ alkyl or together they form the group

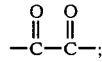

Y is O or S; $X_1$, $X_2$, $X_3$ and $X_4$ are individually H, halogen, $C_1$–$C_3$ alkyl, $C_1$–$C_3$ alkoxy, alkylcarbonyl, alkoxycarbonyl, $C_1$–$C_3$ alkylthio, $NO_2$, CN or $NR_5R_6$ wherein $R_5$ and $R_6$ are H or $C_1$–$C_3$ alkyl with the provisos that at least one of $X_1$, $X_2$, $X_3$ or $X_4$ is other than H and (a) when three of $X_1$, $X_2$, $X_3$ or $X_4$ are H, the fourth substitution cannot be halogen or alkyl, (b) when $X_1$ and $X_3$ are H, $X_2$ and $X_4$ cannot both be halogen, (c) when $X_2$ and $X_3$ are H, $X_1$ and $X_4$ cannot be both halogen, (d) when $X_1$ and $X_4$ are hydrogen, $X_2$ and $X_3$ cannot both be halogen and R is a $C_1$–$C_4$ haloalkyl, haloalkoxy or haloalkylthio group which possess insecticidal properties.

23 Claims, No Drawings

SUBSTITUTED N-AROYL N'-PHENYL UREA COMPOUNDS

CROSS-REFERENCE TO RELATED APPLICATION

This is a continuation, of application Ser. No. 401,493, filed July 26, 1982, now abandoned.

BACKGROUND OF THE INVENTION

This invention relates to novel substituted N-aroyl N'-phenyl ureas, a process for producing them, insecticidal compositions containing them and a method for controlling certain insects.

Various insecticidal derivatives of urea are known in the art, such as, for example, U.S. Pat. Nos. 4,173,638; 4,005,223; 4,170,657; 4,139,636; 4,089,975 and German Patent Application No. 3,003,113.

The N-aroyl N'-phenyl ureas of the present invention are more active and have a broader spectrum of effectiveness than the benzoylurea insecticides currently available.

SUMMARY OF THE INVENTION

The novel compounds of this invention are N-aroyl N'-phenyl ureas having the formula

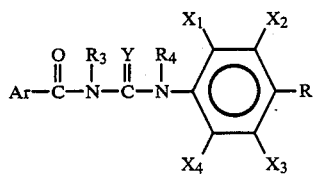

wherein: Ar is a substituted phenyl, pyridyl or pyrimidinyl radical wherein the substituents are chloro, bromo, fluoro $C_1$–$C_3$ alkyl or $C_1$–$C_3$ alkoxy, with the proviso that at least one substituent is positioned ortho to the carbonyl group; $R_3$ and $R_4$ are individually H or $C_1$–$C_4$ alkyl or together they form the group

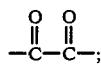

Y is O or S; $X_1$, $X_2$, $X_3$ and $X_4$ are individually H, halogen, $C_1$–$C_3$ alkyl, $C_1$–$C_3$ alkoxy, alkylcarbonyl, alkoxycarbonyl, $C_1$–$C_3$ alkylthio, $NO_2$, CN or $NR_5R_6$ wherein $R_5$ and $R_6$ are H or $C_1$–$C_3$ alkyl with the provisos that at least one of $X_1$, $X_2$, $X_3$ or $X_4$ is other than H and (a) when three of $X_1$, $X_2$, $X_3$ or $X_4$ are H, the fourth substitution cannot be halogen or alkyl, (b) when $X_1$ and $X_3$ are H, $X_2$ and $X_4$ cannot both be halogen, (c) when $X_2$ and $X_3$ are H, $X_1$ and $X_4$ cannot both be halogen, (d) when $X_1$ and $X_4$ are hydrogen, $X_2$ and $X_3$ cannot both be halogen and R is a $C_1$–$C_4$ haloalkyl, haloalkoxy or haloalkylthio group.

These novel compounds can be prepared by methods analogous to those known in the art, e.g., as taught in U.S. Pat. No. 4,139,636.

The invention also provides insecticidal compositions comprising an insecticidally effective amount of the above described N-aroyl N'-phenyl ureas in admixture with a suitable carrier or adjuvant therefore and a method for killing and/or controlling insects which comprises applying the active compound, alone or in admixture with a carrier, to the insects, the insect larvae or their habitats.

Detailed Description of the Invention

The preferred compounds of this invention are those having the formula

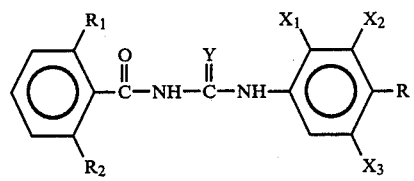

where $R_1$ is F or Cl, $R_2$ is F, Cl or H, Y is O or S, $X_1$ is H, Cl or $CH_3$, $X_2$ and $X_3$ are H, Cl, $CH_3$ or $OCH_3$ and R is $CF_3$, $OCF_3$, $OCF_2CHF_2$, $OCF_2CHClF$ or $OCF_2CHFBr$. Most preferably, $R_1$ and $R_2$ are both fluorine, one of $R_1$ and $R_2$ is F and the other Cl or $R_1$ is Cl and $R_2$ is H, $X_2$ and $X_3$ are methyl and R is $OCF_2CHClF$, $OCF_2CHF_2$ or $OCF_2CHFBr$. Particularly preferred compounds are those wherein $X_1$ and $X_2$ are Cl and $X_3$ is H; $X_1$ and $X_3$ are $CH_3$ and $X_2$ is H; or $X_2$ and $X_3$ are $CH_3$ and $X_1$ is H.

The compounds of the present invention are normally crystalline solids of low solubility in water and of moderate solubility in many organic solvents. The compounds have low phytotoxicity and have exceptional activity in the control of various undesirable agricultural, household and veterinary insect pests.

Representative of the various insects which can be controlled by the active compounds of the present invention are members of the orders Lepidoptera, Coleoptera, Diptera, Orthoptera, Homoptera, Thysanoptera and Acarina. They are active against normally sensitive and resistant species at some stages of development. Examples of insect pests comprising the above include the tobacco budworm (*Heliothis virescens*), the beet armyworm (*Spodoptera exigua*), the Egyptian cotton leafworm (*Spodoptera littoralis*), the American bollworm (*Heliothis armigera*), the diamond-back moth (*Plutella maculipennis*), the gypsy moth (*Lymantria dispar*), the cutworm (*Agrotis segetum*), the Mediterranean flour moth (*Ephestia kuehniella*), the Colorado potato beetle (*Leptinotarsa decimlineata*), the mustard beetle (*Phaedon cochleariae*), the cotton boll weevil (*Anthonomus grandis*), the Mexican bean beetle (*Epilachna varivestis*), the khapra beetle (*Trogoderma granarium*), the housefly (*Musca domestica*), the lesser housefly (*Fannia canicularis*), the Mediterranean fruit fly (*Ceratitis capitata*), the black blow fly (*Phormia regina*), the cabbage rootfly (*Hylemya brassicae*), the yellow fever mosquito (*Aedes aegypti*), the malaria mosquito (*Anopheles stephensi*), the desert locust (*Schistocerca gregaria*), the migratory locust (*Locusta migratoria*), the German cockroach (*Blattells germanica*), the American cockroach (*Periplaneta americana*), the pear psylla (*Psylla pyricola*), the onion thrips (*Thrips tabaci*), and the citrus rust mite (*Phyllocoptruta oleivora*).

The compounds are highly active and can be employed to kill insects outright and/or to prevent adult emergence from juvenile forms of the insect. In such applications, the insect to be controlled and/or its habitat is contacted or treated with an insecticidal amount of one or more of the compounds of the present invention. The compounds may be administered orally to warm blooded animals from which they are excreted unchanged and they effectively combat the larvae of certain feces inhabiting insects, e.g., the face fly, horn fly and buffalo fly.

For all such uses, these compounds can be employed in unmodified form. However, the present invention embraces the use of an insecticidally-effective amount of the active ingredients in composition form with a material known in the art as an adjuvent or carrier.

Thus, for example, compositions employing one or a combination of these active ingredients can be in the form of a liquid or a dust; and the adjuvant employed can be any one of a plurality of materials including aromatic solvents, petroleum distillates, water or other liquid carriers, propellant substances, surface-active dispersing agents, light absorbers and finely-divided carrier solids.

The exact concentration of one or a combination of the compounds of the present invention in a composition thereof with an adjuvant therefore can vary; it is only necessary that one or a combination of the compounds be present in a sufficient amount so as to make possible the application of an insecticidally-effective or inactivating dosage.

Generally, for practical applications, one or a combination of these active ingredients can be broadly applied to the insect larvae or their habitat in compositions containing from about 0.0001 to about 98 percent by weight, preferably 5 to 50 percent by weight, of the compounds.

The invention is further illustrated by the following examples.

EXAMPLE 1—(A) Preparation of 2,6-diethyl-4-nitrophenol

A solution of 45 g (0.3 mole) of 2,6-diethylphenol in 300 ml of chloroform was prepared in a 500 ml, 3-necked round bottom flask fitted with a mechanical stirrer, thermometer and dropping funnel and 27 g (0.3 mole) of 70 percent $HNO_3$ was added dropwise with stirring and cooling at 25°–30° C. in ½ hour. Stirring at room temperature was continued for 5 hours. The mixture was washed with 100 ml of water and the solvent removed in a rotary evaporator. A dark red oil (86 g) was obtained which partially crystallized on standing. This was cooled in an ice water bath and the resulting solid removed by suction filtration. The cake (A) was washed with cold chloroform and dried at room temperature (19 g). NMR indicated the product was 2,6-diethyl-4-nitrophenol (93 percent pure). The solvent was removed from the filtrate in a rotary evaporator leaving 43 g of residue (B). Gas chromatography indicated 47 percent starting material, 22 percent desired product, plus two higher products. (B) was dissolved in 200 ml chloroform, returned to the reactor and 13 ml of $HNO_3$ was added dropwise with stirring in 5 minutes. The temperature rose from 23° to 30° C. Stirring at room temperature was continued for 5 hours and the mixture worked up as above. 62 Grams of a dark red oil (C) was obtained which was placed in the refrigerator overnight. Suction filtration provided 5 grams of solid (D).

(B) Preparation of 4-amino-2,6-diethylphenol.HCl

Cake (A) and solid (D) were combined (24 g) and placed in a Pyrex bottle with 200 ml of 95 percent ethanol and 2 g of 5 percent palladium on carbon catalyst and hydrogenated in a Parr apparatus at 30–50 psig for 2.75 hours using a heat lamp. Hydrogenation almost stopped when 16 psig hydrogen absorbed. Two more grams of catalyst were added and hydrogenation was continued for 1.33 hours when hydrogenation stopped. An additional 20 psig hydrogen absorbed, although there was a small leak in the apparatus. The mixture was cooled and suction filtered to remove the catalyst which was washed with some ethanol. The ethanol was removed from the filtrate in a rotary evaporator. The residue, a brown, oily, low-melting solid, weighed 28 g. The solid was dissolved in 250 ml of methylene dichloride which was then saturated with dry HCl while cooling in an ice water bath. After filtering with suction, the resulting cake was washed with cold methylene dichloride and dried at room temperature. 16 Grams of a tan solid was obtained, m.p. 230°–235° C. The yield was 66 percent and the structure was confirmed by NMR.

(C) Preparation of 4-(2-chloro-1,1,2-trifluoroethoxy)-3,5-diethylbenzenamine

The above tan solid (16 g) was placed in a 500 ml round bottom flask fitted with a mechanical stirrer, thermometer, reflux condenser and sparger, along with 150 ml of dimethylformamide and 9.0 g (0.16 mole) of KOH pellets which were ground to powder. The mixture was heated while stirring to 90° C. and 12 g (0.1 mole) of chlorotrifluoroethylene was bubbled in at 90°–100° C. in 35 minutes. Stirring was continued at about 90° C. for 5 minutes, the mixture was cooled with an ice water bath and 300 ml of cold water was added. The mixture was extracted with 200 ml of methylene dichloride and then 100 ml of methylene dichloride. The extracts were combined, washed with 250 ml of water and the methylene dichloride removed in a rotary evaporator. The residue was distilled through a short column. The second cut (120°–130° C./2 mm) was a light tan viscous liquid weighing 9 g. The structure was confirmed by NMR and the yield was 40 percent.

(D) Preparation of N-(((4-(2-chloro-1,1,2-trifluoroethoxy)-3,5-diethylphenyl)amino)carbonyl)-2,6-difluorobenzamide The light tan liquid prepared above (9 g, 0.03 mole) was dissolved in 150 ml toluene in a 500 ml, 3-necked round bottom flask fitted with a mechanical stirrer, thermometer and reflux condenser and 7.3 g (0.04 mole) of 2,6-difluorobenzoyl isocyanate was added while stirring. The temperature rose from 21° to 26° C. The mixture was heated at reflux for 1 hour and filtered hot through fluted filter paper to remove a trace of dirt. The filtrate was cooled in an ice water bath and the upper solvent layer decanted off about 1 g of a brown gum. The toluene was removed in a rotary evaporator leaving a residue of 17 g of a dark brown viscous oil to which 25 ml of isopropanol was added. Upon heating to boiling, a clear solution developed which was cooled in an ice water bath. The resulting crystals were removed by suction filtration, the filter cake was washed with cold isopropanol and dried at room temperature. A light tan solid (6.5 g, m.p. 122°–124° C.) was obtained. The structure was confirmed by NMR.

Analysis: Calcd: C, 51.68; H, 3.90; N, 6.03. Found: C, 51.5; H, 3.93; N, 6.04

Employing the above procedures and appropriate starting materials, the following compounds were prepared:

N-(((4-(1,1,2,2-Tetrafluoroethoxy)-3,5-dimethylphenyl)amino)carbonyl)-2,6-difluorobenzamide.
  M.P. 190°–192° C.

Analysis: Calcd: C, 51.43; H, 3.36; N, 6.67 Found: C, 51.30; H, 3.45; N, 6.59

N-(((4-(1,1,2,2-Tetrafluoroethoxy)-3,5-dimethylphenyl)amino)carbonyl)-2-chlorobenzamide.
M.P. 165°–167° C.
Analysis: Calcd: C, 51.62; H, 3.61; N, 6.69 Found: C, 51.9; H, 3.60; N, 6.67

N-(((4-(2-Chloro-1,1,2-trifluoroethoxy)-3,5-dimethylphenyl)amino)carbonyl)-2,6-difluorobenzamide.
M.P. 184°–186° C.
Analysis: Calcd: C, 49.50; H, 3.23; N, 6.42 Found: C, 49.60; H, 3.18; N, 6.38

N-(((4-(2-Chloro-1,1,2-trifluoroethoxy)-3,5-dimethylphenyl)amino)carbonyl)-2-chlorobenzamide.
M.P. 152°–154° C.
Analysis: Calcd: C, 49.67; H, 3.47; N, 6.44 Found: C, 49.70; H, 3.45; N, 6.34

In addition to the above described preparative methods, many of the compounds of this invention can be made by reacting a compound having the formula

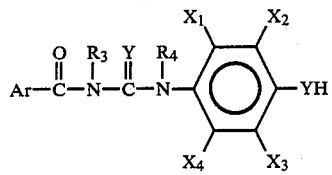

wherein all of the substituents are as above defined, with a haloalkene as is known in the art.

The biological activity of several of these compounds was determined. In the best armyworm test, cotton leaves were dipped in aqueous suspensions of the chemicals, dried, excised and placed into petri dishes with five second-instar beet armyworm (*Spodoptera exigua*) larvae. Mortality counts were made five days later. The tobacco budworm test was the same except that five tobacco budworm (*Heliothis virescens*) larvae were placed onto the treated leaves. The results are summarized below:

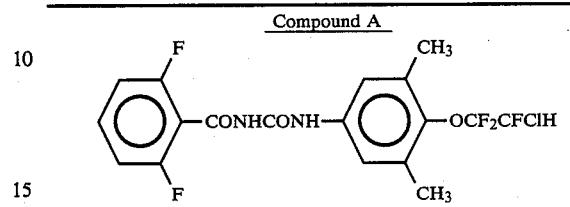

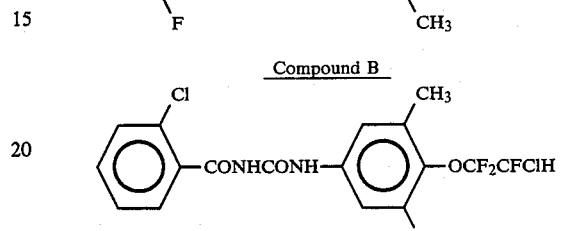

| Compound | Percent Control at Indicated Dosage, ppm Tobacco Budworm Test | | |
|---|---|---|---|
| | 50 | 12.5 | 3.1 |
| A | 100 | 100 | 92 |
| B | 100 | 100 | 33.3 |

Employing the above described preparative and testing methods, the compounds listed in the following table were prepared and tested. The test results, $LD_{90}$ ppm, indicate the dosage necessary to obtain 90 percent kill of the indicated insect.

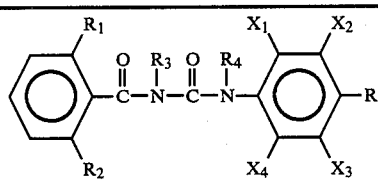

| Ex. No. | $R_1$ | $R_2$ | $R_3$ | $R_4$ | $X_1$ | $X_2$ | $X_3$ | $X_4$ | R | Melting Point °C. | $LD_{90}$, ppm Beet Armyworm | Tobacco Budworm |
|---|---|---|---|---|---|---|---|---|---|---|---|---|
| 1 | F | F | H | H | Cl | Cl | H | H | OCF$_2$CHFCl | 180–182 | 0.6 | 2.5 |
| 2 | F | F | H | H | Cl | Cl | H | H | OCF$_2$CHF$_2$ | 166–169 | | 12.5 |
| 3 | F | F | H | H | Cl | Cl | H | H | OCF$_2$CHFBr | 169–171 | 1.6 | 1.6 |
| 4 | F | F | H | H | CH$_3$ | CH$_3$ | H | H | OCF$_2$CHFCl | 169–171 | | |
| 5 | Cl | H | H | H | CH$_3$ | CH$_3$ | H | H | OCF$_2$CHFCl | 150–152 | | |
| 6 | F | F | H | H | CH$_3$ | H | CH$_3$ | H | OCF$_2$CHF$_2$ | | | |
| 7 | F | F | H | H | CH$_3$ | H | CH$_3$ | H | OCF$_2$CHFCl | 143–145 | | 3.1 |
| 8 | F | F | H | H | CH$_3$ | H | CH$_3$ | H | OCF$_2$CHFBr | | | |
| 9 | Cl | H | H | H | CH$_3$ | H | CH$_3$ | H | OCF$_2$CHFCl | 157–159 | | 12.5 |
| 10 | F | Cl | H | H | CH$_3$ | H | CH$_3$ | H | OCF$_2$CHFCl | 145–147 | | 12.5 |
| 11 | F | F | H | H | CH$_3$ | H | H | CH$_3$ | OCF$_2$CHFCl | 191–193 | | |
| 12 | F | F | H | H | H | CH$_3$ | CH$_3$ | H | OCF$_2$CHF$_2$ | 190–192 | | 3.1 |
| 13 | F | F | H | H | H | CH$_3$ | CH$_3$ | H | OCF$_2$CHFCl | 184–186 | 1.2 | 1.2 |
| 14 | F | F | H | H | H | CH$_3$ | CH$_3$ | H | OCF$_2$CHFBr | 176–178 | 3.1 | 3.1 |
| 15 | Cl | H | H | H | H | CH$_3$ | CH$_3$ | H | OCF$_2$CHF$_2$ | 165–167 | 12.5 | 12.5 |
| 16 | Cl | H | H | H | H | CH$_3$ | CH$_3$ | H | OCF$_2$CHFCl | 152–154 | 5.0 | 12.5 |
| 17 | Cl | H | H | H | H | CH$_3$ | CH$_3$ | H | OCF$_2$CHFBr | 147–149 | 6.2 | 25.0 |
| 18 | F | Cl | H | H | H | CH$_3$ | CH$_3$ | H | OCF$_2$CHF$_2$ | | | |
| 19 | F | Cl | H | H | H | CH$_3$ | CH$_3$ | H | OCF$_2$CHFCl | | | |
| 20 | F | Cl | H | H | H | CH$_3$ | CH$_3$ | H | OCF$_2$CHFBr | | | |
| 21 | F | F | H | H | H | C$_2$H$_5$ | C$_2$H$_5$ | H | OCF$_2$CHFCl | 122–124 | 25.0 | 25.0 |
| 22 | F | F | H | H | CH$_3$ | CH$_3$ | CH$_3$ | H | OCF$_2$CHF$_2$ | | | |
| 23 | F | F | H | H | CH$_3$ | CH$_3$ | CH$_3$ | H | OCF$_2$CHFCl | 152–154 | 3.1 | 3.1 |
| 24 | F | F | H | H | CH$_3$ | CH$_3$ | CH$_3$ | H | OCF$_2$CHFBr | | | |
| 25 | F | F | H | H | CH$_3$ | CH$_3$ | CH$_3$ | CH$_3$ | OCF$_2$CHF$_2$ | | | |
| 26 | F | F | H | H | H | OCH$_3$ | OCH$_3$ | H | OCF$_2$CHFCl | 142–144 | 10.0 | 10.0 |

-continued

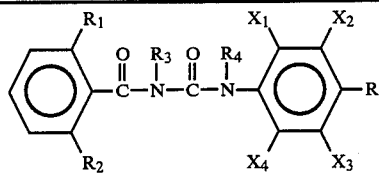

| Ex. No. | R₁ | R₂ | R₃ | R₄ | X₁ | X₂ | X₃ | X₄ | R | Melting Point °C. | LD₉₀ ppm Beet Armyworm | Tobacco Budworm |
|---|---|---|---|---|---|---|---|---|---|---|---|---|
| 27 | F  | F  | H | H | CH₃ | H  | Cl  | H   | OCF₂CHF₂  |         |     |  |
| 28 | F  | F  | H | H | CH₃ | H  | Cl  | H   | OCF₂CHFCl | 178–180 |     |  |
| 29 | Cl | H  | H | H | CH₃ | H  | Cl  | H   | OCF₂CHFCl |         |     |  |
| 30 | Cl | H  | H | H | H   | Cl | CH₃ | H   | OCF₂CHFCl |         |     |  |
| 31 | F  | F  | H | H | H   | Cl | CH₃ | H   | OCF₂CHFCl | 175–177 |     |  |
| 32 | F  | F  | H | H | CH₃ | Cl | Cl  | H   | OCF₂CHF₂  |         |     |  |
| 33 | F  | F  | H | H | CH₃ | Cl | Cl  | H   | OCF₂CHFCl | 190–192 |     |  |
| 34 | F  | F  | H | H | CH₃ | Cl | Cl  | H   | OCF₂CHFCl | 167–169 |     |  |
| 35 | F  | F  | H | H | CH₃ | Cl | Cl  | CH₃ | OCF₂CHFCl | 240–241 |     |  |
| 36 | F  | F  | H | H | H   | OCCH₃ (O=) | CH₃ | H | OCF₂CHFCl | 163–165 |     |  |
| 37 | F  | F  | H | H | H   | OCOCH₃ | CH₃ | H | OCF₂CHCl₂ | 153–155 |     |  |
| 38 | Cl | H  | H | H | H   | OCOCH₃ | CH₃ | H | OCF₂CHCl₂ | 143–145 |     |  |
| 39 | F  | F  | H | H | H   | NO₂ | H  | H   | OCF₂CHFCl | 227–228 |     |  |
| 40 | Cl | H  | H | H | H   | NO₂ | H  | H   | OCF₂CHFCl | 206–208 |     |  |
| 41 | F  | Cl | H | H | CH₃ | Cl  | Cl | CH₃ | OCF₂CHFCl | 228–229 |     |  |
| 42 | F  | F  | H | H | Cl  | Cl  | Cl | H   | OCF₂CHCl₂ | 181–183 | 5.0 |  |
| 43 | F  | F  | H | H | Cl  | Cl  | Cl | H   | OCF₂CHF₂  |         |     |  |
| 44 | F  | F  | H | H | Cl  | Cl  | Cl | H   | OCF₂CHFCl |         |     |  |
| 45 | F  | F  | H | H | Cl  | Cl  | Cl | H   | OCF₂CHFBr |         |     |  |

In further embodiments, the compounds of the present invention or compositions containing the same, can be advantageously employed in combination with one or more additional pesticidal compounds. Such additional pesticidal compounds may be insecticides, nematocides, acaricides, herbicides, fungicides or bactericides that are compatible with the compounds of the present invention in the medium selected fo application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

The compounds of this invention are, or tend to be, slow acting, i.e., they disrupt the molting of the insect, thereby killing it. As a result, some time can pass before the insects are killed. Accordingly, an increased benefit can be obtained by combining the compounds of this invention with quicker acting insecticides such as, for example, organophosphorus compounds, carbamates and pyrethroids. Because of this different mode of action, the compounds of this invention kill or control insects which have, or may be developing, resistance to the more common insecticides and thus they inhibit or delay the development of resistance to such insecticides.

Various modifications may be made in the present invention without departing from the spirit or scope thereof and it is understood that we limit ourselves only as defined in the appended claims.

We claim:
1. A compound having the formula

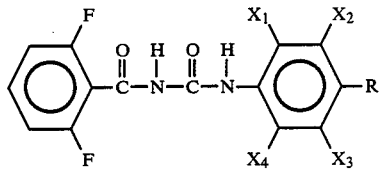

wherein $X_1$, $X_2$, $X_3$ and $X_4$ are individually H, Cl or CH₃ with the proviso that at least two of $X_1$, $X_2$, $X_3$ and $X_4$ are other than H and at least one is CH₃ and R is haloalkoxy.

2. Compound of claim 1 wherein R is OCF₃, OCF₂CHCl₂, OCF₂CHF₂, OCF₂CHFCl, OCF₂CHFBr, OCF₂CHFI or OCFClCHFCl.

3. Compound of claim 2 wherein R is OCF₂CHF₂, OCF₂CHFCl or OCF₂CHFBr.

4. Compound of claim 3 wherein $X_1$ is H, $X_2$ and $X_3$ are both CH₃ and R is OCF₂CHFCl.

5. Compound of claim 3 wherein $X_1$ is H, $X_2$ and $X_3$ are both CH₃ and R is OCF₂CHF₂.

6. Compound of claim 3 wherein $X_1$ is H, $X_2$ and $X_3$ are both CH₃ and R is OCF₂CHFBr.

7. Compound of claim 3 wherein $X_1$ and $X_3$ are both CH₃, $X_2$ is H and R is OCF₂CHF₂, OCF₂CHFCl or OCF₂CHFBr.

8. Compound of claim 3 wherein $X_1$, $X_2$ and $X_3$ are $CH_3$ and R is $OCF_2CHF_2$, $OCF_2CHFCl$ or $OCF_2CHFBr$.

9. Compound of claim 3 wherein $X_1$ is methyl and $X_2$ and $X_3$ are chloro.

10. A method of killing and/or controlling insects which comprises applying to the insects, the insect larvae or their habitats an insecticidally effective amount of a compound having the formula

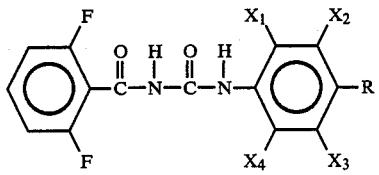

wherein $X_1$, $X_2$, $X_3$ and $X_4$ are individually H, Cl or $CH_3$ with the proviso that at least two of $X_1$, $X_2$, $X_3$ and $X_4$ are other than H and at least one is $CH_3$ and R is haloalkoxy.

11. Method of claim 10 wherein R is $OCF_2CHF_2$, $OCF_2CHFCl$ or $OCF_2CHFBr$.

12. Method of claim 11 wherein $X_1$ and $X_3$ are both $CH_3$ and $X_2$ is H.

13. Method of claim 11 wherein $X_2$ and $X_3$ are both $CH_3$ and $X_1$ is H.

14. Method of claim 11 wherein $X_1$, $X_2$ and $X_3$ are all $CH_3$.

15. A composition comprising an insecticidally effective amount of at least one compound having the formula

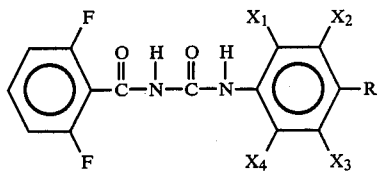

wherein $X_1$, $X_2$, $X_3$ and $X_4$ are individually H, Cl or $CH_3$ with the proviso that at least two of $X_1$, $X_2$, $X_3$ and $X_4$ are other than H and at least one is $CH_3$ and R is haloalkoxy.

16. Composition of claim 15 wherein R is $OCF_3$, $OCF_2CHCl_2$, $OCF_2CHF_2$, $OCF_2CHFCl$, $OCF_2CHFBr$, $OCF_2CHFI$ or $OCFClCHFCl$.

17. Composition of claim 16 wherein R is $OCF_2CHF_2$, $OCF_2CHFCl$ or $OCF_2CHFBr$.

18. Composition of claim 16 wherein $X_1$ is H, $X_2$ and $X_3$ are both $CH_3$ and R is $OCF_2CHFCl$.

19. Composition of claim 16 wherein $X_1$ is H, $X_2$ and $X_3$ are both $CH_3$ and R is $OCF_2CHF_2$.

20. Composition of claim 16 wherein $R_1$ and $R_2$ are both F, $X_1$ is H, $X_2$ and $X_3$ are both $CH_3$ and R is $OCF_2CHFBr$.

21. Composition of claim 16 wherein $X_1$ and $X_3$ are both $CH_3$, $X_2$ is H and R is $OCF_2CHF_2$, $OCF_2CHFCl$ or $OCF_2CHFBr$.

22. Composition of claim 16 wherein $X_1$, $X_2$ and $X_3$ are $CH_3$ and R is $OCF_2CHF_2$, $OCF_2CHFCl$ or $OCF_2CHFBr$.

23. Composition of claim 16 wherein $X_1$ is methyl and $X_2$ and $X_3$ are chloro.

* * * * *